United States Patent [19]

Scuitto et al.

[11] Patent Number: 4,845,041

[45] Date of Patent: Jul. 4, 1989

[54] ATOMIC-ABSORPTION SPUTTERING CHAMBER AND SYSTEM

[75] Inventors: Thomas J. Scuitto, Talent; Theodore J. Scuitto, Grants Pass; Al E. Bernhard, Brookings, all of Oreg.

[73] Assignee: Analyte Corporation, Grants Pass, Oreg.

[21] Appl. No.: 799,918

[22] Filed: Nov. 20, 1985

[51] Int. Cl.$^4$ .......................................... G01N 21/76
[52] U.S. Cl. ................................. 436/172; 436/171; 204/192.1; 204/298
[58] Field of Search ................... 204/298, 192, 192 R; 436/171, 172

[56] References Cited

U.S. PATENT DOCUMENTS

| | | | |
|---|---|---|---|
| 4,036,167 | 7/1977 | Lu | 204/298 |
| 4,101,772 | 7/1978 | Konishi et al. | 204/298 |
| 4,134,817 | 1/1979 | Bourdon | 204/298 |
| 4,172,020 | 10/1979 | Tiscone et al. | 204/298 |
| 4,302,311 | 11/1981 | Lowe et al. | 204/298 |
| 4,358,686 | 11/1982 | Kinoshita | 204/298 |

FOREIGN PATENT DOCUMENTS 0163586 10/1954 Australia .
0414987 11/1970 Australia .
0482264 6/1976 Australia .

OTHER PUBLICATIONS

Gough, D. S. Direct Analysis of Metals & Alloys by AAS Analytical Chem. 48, Nov. 13, 1976, p. 1926.

Primary Examiner—Kenneth M. Schor
Assistant Examiner—L. Johnson
Attorney, Agent, or Firm—Ashen Golant Martin & Seldon

[57] ABSTRACT

Gas from angled jets in a conical array bounces off the sample in a high-pressure stream, effectively centered in a duct leading to an optical-measurement chamber. A glow discharge, in the high-pressure zone where gas hits the sample, provides effective sample bombardment. Pulsed high-energy presputtering quickly bares the sample interior for analysis. Dislodged atoms flow with the gas (whose centering keeps an arrestor recess clear or obviates the need for a recess) to the measurement chamber, where the stream is bent into a long path for coaxial measurement viewing. To lessen turbulence losses, a contoured guide leads the stream into the coaxial path. The stream can be split into two opposed substreams to double the absorption pathlength. Discharge current is adjusted to use a linear part of the absorbance curve; or servocontrolled to hold absorbance at an ideal value—the current itself serving as an index of concentration. A water-cooled cathode plate firmly contacts the front of the sample (around the sputter area). The arrestor is mounted resiliently: it too makes firm sample contact. Servocontrol of gas pumping and/or supply rate stabilizes pressure, absorbance, or both. Emission is monitored to normalize (or prevent) sputtering-rate variations. A baffle in the optical chamber deters atomic coating of end windows.

46 Claims, 10 Drawing Sheets

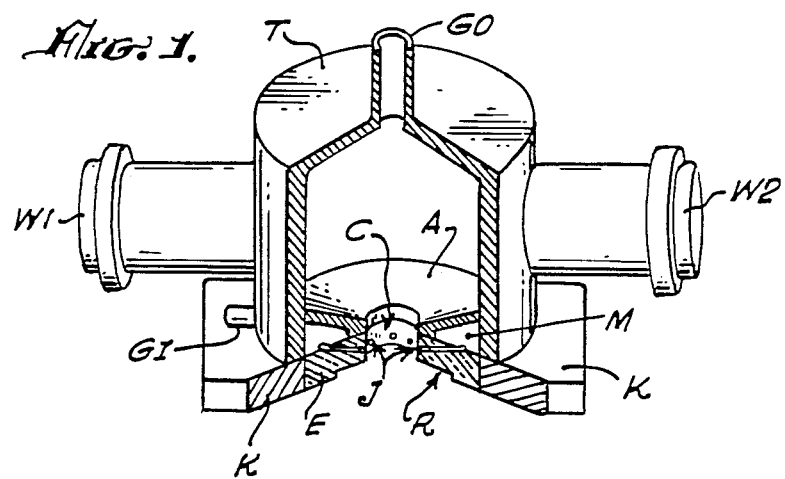
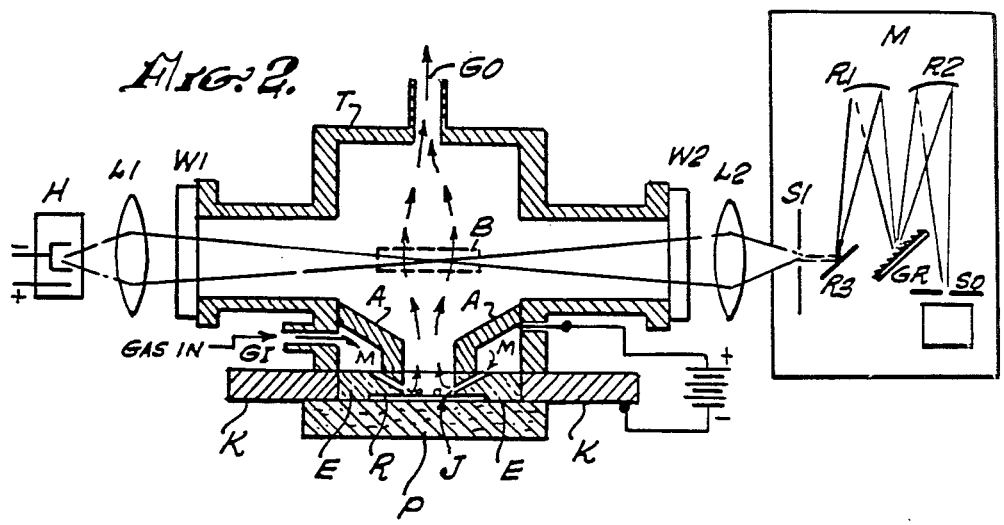

ATOMIC-ABSORPTION SPUTTERING CHAMBER AND SYSTEM

BACKGROUND

1. Field of the Invention

This invention relates generally to atomic-fluorescence and atomic-absorption spectroscopy; and more particularly to improved apparatus and methods for disassociating solid materials such as metal or powdered rock into free atoms—and for bringing such free atoms conveniently into a light path and precisely, accurately measuring their absorption or fluorescence.

Such measurements are useful for chemical analysis. Certain portions of the invention are useful in supplying free atoms for any purpose, but particularly in replacing the burner of a typical atomic-absorption spectrophotometer so that solid samples may be analyzed directly without the sample dissolution that historically has been required.

2. Prior Art

A commonly used instrumental analysis method for elemental analysis of various materials, for trace and minor elements, is the atomic-absorption method.

FIG. 15 represents schematically the usual instrumentation, consisting of apparatus such as a nebulizer 1 for generating a vapor, a burner assembly 2 to disassociate into free atoms 4 the vapor delivered by the nebulizer, a hollow-cathode lamp 3 or like source of monochromatic light which is directed through the atomized vapor 4, and a device 5 for isolating and measuring the intensity of that fraction of the monochromatic light that passes through the atomized vapor.

Quantitative measurement of elements present in the vapor, and thus of the sample from which the vapor was derived, is made by comparing the intensity of the monochromatic light characteristic of an element after absorption in the burner flame to the unabsorbed intensity of the light source.

Although it is a highly sensitive analytical method, atomic-absorption spectrometry has suffered from two major handicaps:

(a) With one exception outlined below, it has generally been considered necessary to prepare samples in liquid form, for presentation to the burner flame. This has required that solid material such as metals, rock, etc. be dissolved in appropriate acid solutions—entailing much time and effort.

Sputtering of free atoms in a gaseous glow discharge has been previously demonstrated, but has been practical only for atomic-emission elemental analysis and for other applications such as coating of thin metal films on a substrate.

The exception is a development project of the Australian Scientific and Industrial Research Organization (CSIRO), which did include attempts to use the sputtering process for atomic-absorption or atomic-fluorescence analysis, as reported in *Analytical Chemistry* 48 13, November 1976 (page 1926), and Australian Pat. No. 482,264.

The reported performance data from CSIRO—that is, the sputtering rate, sensitivity, stability, dynamic range and speed of analysis—indicate that without significant improvements in these parameters the technique was not fully practical.

(b) The inherent nature of the atomic-absorption process provides a linear relationship between concentration and measured absorbance over only a very small range of concentration. Because of this, dynamic range is limited to about two orders of magnitude.

In many cases this requires successive dilutions of the same sample, and multiple analyses, to cover the dynamic range required.

The CSIRO apparatus appears in FIGS. 16 through 18. This device replaces only the nebulizer 1 and burner 2 of FIG. 15, being employed with a generally comparable source, monochromator, and imaging system (not illustrated in FIGS. 16 through 18).

As shown in FIG. 16, the CSIRO device includes a gas-tight chamber 11, with optical-quality end windows 12 for passage of the measurement light beam generally along a central path 18. (The barrel of the chamber 11 is illustrated broken away as at 13 and 14 to permit showing the apparatus at a fairly large scale.) A pumping outlet 15 is provided for evacuation of the chamber 11, and thereafter for continuous drawing-off of the working gas. An anode 16 is sealed through the chamber wall for formation of a glow discharge in the chamber.

Serving as cathode for that discharge is the surface 41 of the specimen or sample 24. The sample 24 is accessible for this purpose through the side of the chamber 11 opposite the pump 15 and anode 16. Positive ions of the working gas are accelerated through the "dark space" or "cathode fall" region of the glow discharge toward the negatively charged active surface 41 of the sample 24. These positive ions energetically bombard the surface 41 and thereby dislodge or "sputter" atoms from that surface into the chamber.

Behind the sample 24 is a water-jacketed cooling member 25. Typically this member 25 is in intimate thermal and electrical contact with the sample 24, simultaneously drawing off heat generated by the glow discharge and establishing the cathodic potential of the sample 24. (Thus in some literature the member 25 may be referred to as the "cathode.")

The forward surface 41 of the sample is pressed or otherwise sealed against its port 17, through the intermediary of a hollow silica annulus 19 (FIGS. 16 through 18). An inert working gas such as argon is introduced into the chamber 11 through a supply tube 21 and through the annulus 19. The supply tube 21 enters the chamber at any convenient point 22 in the wall and exits at a point 24 that is quite near the sample, and in fact is aligned with a mating port 24' in the annulus 19 (see FIG. 17).

The annulus 19 directs the gas supply directly into the sample region and helps confine the discharge. As seen in FIG. 17, the annulus is made in two parts 26, 33 to permit provision of an annular manifold cavity 27 that communicates with the port 24'. A narrow slit 28 completely around the inside diameter 29, 32 of the annulus directs a sheath of high-velocity gas (see FIG. 18) from the manifold 27 into the region in front of the sample surface 41.

Sputtered sample atoms from the sample surface 41 move into the absorption zone—i.e., along the optical path 18—partially carried along in this gas stream and partially through the diffusion process.

The shallow recess 31 at the sample surface 41 prevents electrical breakdown at the annulus, because the recess is shallower than the length of the "dark space" or "cathode fall" region of a glow discharge. The annulus consequently is sometimes instead known as a "discharge arrestor."

If gas velocity at the mouth of the recess is not high enough, the shallow recess 31 tends to clog rapidly: diffusion of sputtered atoms into this region builds up a mound of previously sputtered sample material 43 (FIG. 18) on the sample 41, quickly leading to shorting-out of the dark-space region. This "short circuit" extinguishes the glow and damages the annulus. To keep this system operating, therefore, the annulus must be cleaned frequently.

Similarly diffusion of atoms in the measurement chamber, though essential for atomic-absorption measurements, causes problems: the diffusing atoms are continuously deposited on surfaces of the apparatus, diminishing the supply of free atoms for measurement purposes. Worse yet, some of the atoms are deposited on the optical windows, obscuring the measurement light beam and progressively degrading the signal-to-noise ratio of the measurement.

Yet another source of measurement imprecision arises from the surface character of typical specimens. In previous attempts to use sputtering techniques to provide atoms for absorption or fluorescence analysis, it has been awkward to obtain a representative sampling from the bulk of the specimen material. It has been found necessary to "sputter through" surface imperfections, surface chemical compounds such as oxides, and other surface phenomena to reach atoms free of these effects.

Prior workers have accomplished this by operating the sputtering discharge for a relatively long time before taking measurements considered to represent the bulk material. Preliminary measurement values can be monitored during this protracted cleaning, to assess the progress of the cleaning operation itself: representative bulk material has been reached when the observed readings come to equilibrium. This approach results in prohibitively long analysis times.

BRIEF SUMMARY OF THE DISCLOSURE

Our invention optimally encompasses provision of several novel features in conjunction. These several novel features, however, are also each valuable and capable of enhancing performance of an atomic-absorption or atomic-fluorescence system when implemented individually—or in various combinations of fewer than all the features.

Consequently our invention must be understood to have a large number of embodiments. The principal preferred embodiments will be outlined here.

A first preferred embodiment of our invention is an apparatus for sputtering atoms from a solid-sample surface for atomic-absorption measurements. The apparatus must include some means for receiving and supporting the sample. For purposes of generality, we will refer to these means as the "receiving and supporting means."

This first embodiment must also include some means for supplying a stream of gas, and for directing the stream toward the sample surface from the periphery of that surface. Again for the sake of generality we will call these the "supplying and directing means," and analogous terminology will be used throughout this document.

This embodiment also includes some means for drawing the stream of gas away from the sample surface. This embodiment also includes means, including an anode, for forming an electrical discharge in the gas, between the sample surface and the anode. The discharge is formed to sputter sample atoms out of the sample surface, for motion with the gas stream flowing away from the surface.

In this first embodiment, the supplying and directing means direct the gas stream at a substantial nonzero angle of inclination toward the sample surface. These means include at least one jet disposed adjacent to the sample surface and pointing at a substantially nonzero angle toward the surface.

We consider it preferable or advantageous, in this first embodiment of our invention, that the supplying and directing means include at least three jets disposed about the periphery of the sample surface in a generally conical array, to direct the gas in at least three substreams meeting generally centrally at the sample surface. These substreams deflect each other to form the gas stream flowing away from the sample surface.

In one preferred arrangement the three or more jets are substantially symmetrically disposed, and the substreams deflect each other very generally along the axis of the array. In this way the substreams orient the gas stream flowing away from the sample surface very generally along the axis. In fact, by use of this configuration the gas stream flowing away from the sample surface, and the electrical discharge in the gas stream, are effectively confined to a region very generally along the axis. This confinement may have several beneficial effects, as will be seen shortly.

Still with reference to the first embodiment of our invention, that embodiment may advantageously include a spacer or discharge arrestor disposed in front of the sample surface. The spacer or arrestor has an aperture for passage of the gas stream flowing away from the sample surface. There are two variants of this feature, depending upon whether the element under discussion is actually an arrestor or merely a spacer.

If the element is an arrestor, its aperture is substantially circular and has two sections of different diameters: one of the sections is substantially in contact with the sample surface and has the larger of the two diameters, and the other of the sections is spaced from the sample surface. The spacing, however, is by a distance that is much smaller than the minimum length of a glow discharge. Thus, as in the CSIRO device described earlier, the arrestor forms with the sample surface an annular recess in which no glow discharge can exist.

Now it can be seen that if the element just in front of the sample surface is an arrestor with an annular recess, the axial confinement described above (resulting from the use of mutually deflected symmetrical jets) will minimize sputtering of the atoms into the annular recess. Thereby our invention, in contrast with the prior art, deters blocking of the annular recess by atoms sputtered from the sample surface.

On the other hand, the axial confinement has another advantage—namely, that the element just in front of the sample surface need not have an annular recess at all; that is, the element can be simply a spacer which separates the anode from the sample (cathode) surface to permit a potential difference to be present. That is to say, if the element is a spacer, the advantage of axial confinement of the gas stream is that the basic geometry (use of a nonarresting spacer) becomes permissible.

In either case, the mutually deflected symmetrical jets also help to minimize loss of atoms by deposition on the apparatus.

Now we turn to a second preferred embodiment of our invention—also an apparatus for sputtering atoms from a solid-sample surface for atomic-absorption measurements.

Certain elements of this second embodiment will be familiar: it includes receiving and supporting means for a solid sample; means for supplying a stream of gas and directing the stream toward the sample surface from the periphery and for drawing the gas stream away from the surface—in this case, to flow along a path that is very generally normal to that surface; means for forming a discharge in the gas between the sample and an anode, to sputter atoms out of the surface for motion with the gas stream; and finally, means for projecting a beam of light through the gas stream flowing away from the surface, and for detecting the beam intensity after passage through that gas stream.

Next, this embodiment has some means for bending the stream of gas flowing away from the sample surface, and the atoms that are in motion with that gas stream, from the first-mentioned (generally normal) path into a second path that has an axis which is *not* very generally normal to the sample surface.

Finally, the second embodiment includes some means for projecting a beam of light very generally along the axis of the second path, for passage through the gas stream flowing along the second path; and some means for detecting the intensity of the light beam after passage through the gas stream. Preferably, but not necessarily, the second path is generally parallel to the sample surface.

It is preferable or advantageous, still referring to the second embodiment, that the bending means include a solid guide surface. The guide surface should be disposed to define the first and second paths and to deflect the stream of gas flowing from the sample surface (and, again, the atoms in motion with the gas stream) from the first path into the second path. Preferably this guide surface is generally continuously contoured; and preferably it has an aperture along the axis for passage of the beam of light between the projecting and detecting means via the second path.

Referring once again to the second embodiment, we consider it preferable that the second path be bifurcated—that is, that it have two legs extending in mutually opposite (or at least substantially opposite) directions away from the first path. In operation of this preferred variant of the second embodiment, the stream flowing away from the sample surface splits into two substreams, each substream flowing along one of the two legs, respectively; and the projecting means project the beam of light through both substreams.

Now turning to a third embodiment of our invention, that embodiment too has certain features in common with those already described: it is an apparatus for making atomic-absorption measurements, and it includes receiving and supporting means for a solid sample.

This third embodiment also includes means for providing a stream of gas adjacent the sample; and means, including an anode and a voltage supply, for forming an electrical current discharge in the gas stream between the sample and the anode. The discharge sputters atoms out of the sample into the gas stream and so forms a composite stream of gas and atoms.

Like the previously described embodiments, the third includes means for projecting a beam of light through the stream of gas and atoms, and for detecting the intensity of the beam of light after its passage through the gas stream.

The third embodiment also has means for determining the absorbance of the light beam by the composite stream, using the detected intensity of the beam after passage through the composite stream. These absorbance-determining means have a calibration curve which includes a portion that is generally linear and at least one portion that is generally nonlinear.

Finally, the third embodiment of our invention includes some means for substantially continuously adjusting the current in the discharge to cause the determined absorbance to be in the generally linear portion of the calibration curve. (In some circumstances control of voltage or power may be used instead of current control.)

In this third embodiment, preferably the current-adjusting means include means for varying the effective impedance of the voltage supply. As an example, advantageously the impedance-varying means may include a variable resistance that is effectively in series with the voltage discharge.

The third embodiment of our invention also preferably includes some means for limiting the spectral waveband of the beam of light to which the detector responds; and some means for varying the nominal wavelength of the beam of light substantially continuously while displaying or recording the absorbance.

The result, as will be plain to those skilled in the art, is an atomic-absorption spectrum of the sputtered sample—but particularly a spectrum that is recorded in the generally linear portion of the instrument calibration curve.

Now we will describe a fourth embodiment of our invention. This embodiment is an atomic-absorption apparatus for use with a solid sample and it includes means for receiving and supporting such a solid sample.

It also includes means for providing gas adjacent the sample; and means, including an anode and a voltage supply, for forming an electrical current discharge in the gas between the sample and the anode, to sputter atoms out of such sample into the gas and form a composite of gas and sample atoms.

This embodiment also includes means for projecting a beam of light through the composite and for detecting the intensity of the beam after passage through the composite; and means for determining the absorbance of the light beam by the composite, using the detected intensity of the beam after passage through the composite.

A distinguishing feature of this fourth embodiment is the inclusion of some means substantially continuously adjusting the current in the discharge to hold the determined absorbance at a particular value, and means for displaying or recording the current. These latter means will be called "utilization means." It will be understood that in this embodiment the current is itself used as a measure of the concentration of some constituent in the sample.

As will be clear to those skilled in the art of controlling the current through an electrical discharge, the current-adjusting means may include means for varying the effective impedance of the voltage supply. The impedance-varying means may advantageously include a variable resistance that is effectively in series with the voltage discharge. The utilization means may either display or record a parameter derived from the current, as a measure of concentration of such sample.

The fourth embodiment that is here under discussion preferably also includes means for limiting the spectral waveband of the beam of light to which the detector responds, and for selecting the nominal wavelength of that beam. In addition this embodiment includes means for continuously varying the selection of nominal wavelength while displaying or recording (or both) the discharge current. The apparatus thus displays and/or records a spectrum that is related to an atomic/absorption spectrum of the sample.

A fifth embodiment of our invention is an apparatus for sputtering atoms from a solid-sample surface for atomic-absorption measurements. This embodiment includes solid-sample receiving and supporting means. It also includes a cathode that has a rear side which is adapted to contact the periphery of the sample surface. The cathode also has a front side, and an aperture that passes entirely through the cathode.

This fifth embodiment also includes a spacer fitted within the cathode aperture. The spacer has a rear side that is adapted to contact the sample surface, and has a front side. The spacer also has an aperture that passes entirely through the spacer; the spacer also has within it a conduit for passage of gas from a gas supply toward the sample surface.

The fifth embodiment also has an anode. The anode has a rear side that faces the respective front sides of the cathode and spacer. The anode has aperture that is generally aligned with the aperture in the spacer. Another component of this fifth embodiment is an insulator that is interposed between the cathode and anode.

Finally, the fifth embodiment includes a compliant member that is interposed between the spacer and the anode, and that urges the spacer toward the sample surface. By virtue of this compliant member, the cathode and spacer both closely contact the sample surface—despite normal production tolerances of the cathode, anode, insulator and spacer, as well as normal surface-finishing irregularities of the sample surface.

Preferably the compliant member is an O-ring, and it may be very simply fitted in an O-ring groove that is formed in the back side of the anode.

In this fifth embodiment, typically the electrical discharge generates heat that raises the respective temperatures of the sample, spacer, and cathode. The embodiment preferably further includes some means for lowering the temperature of the cathode to draw away the heat and cool the periphery of the sample surface. It may thus be seen that the compliant member serves an additional important function—namely, accommodation of the dimensional and geometric changes due to variations in respective temperatures of the cathode, spacer, insulator and sample.

Now we will turn to a sixth embodiment of our invention—also an apparatus for sputtering atoms from the surface of a solid sample and making atomic-absorption measurements with the sputtered atoms. This embodiment includes an optical-measurement chamber, and some means for receiving and supporting a solid sample with the sample surface facing into the chamber. It also includes some means for continuously directing a stream of the gas within the chamber from a gas supply to the sample surface.

The sixth embodiment also provides some means, including an anode, for forming an electrical discharge in the gas between the sample surface and the anode, to form and bombard the surface with gas ions and sputter sample atoms from the surface; and means for projecting a beam of light through the sputtered atoms and for making measurements of the optical absorbance by the sputtered atoms.

In addition this embodiment includes a variable-speed device for substantially continuously drawing off the gas from the chamber, and means for automatically controlling the speed at which the gas is drawn off, to optimize the measurements.

There are at least two preferred forms of this sixth embodiment. In one, the apparatus also includes some means for monitoring pressure within the chamber, and the speed-controlling means are responsive to the pressure-monitoring means. The speed-controlling means are caused to operate in such a way as to maintain the pressure at least approximately constant. In the second preferred form of this embodiment, the speed-controlling means are responsive to the measured value of optical absorbance, to maintain the measurements in an optimum absorbance range.

A seventh embodiment of our invention also includes an optical-measurement chamber, and has means for receiving and supporting a solid sample with the sample surface facing into the chamber. The seventh embodiment further includes variable-rate means for continuously directing a stream of gas within the chamber from a gas supply to the sample surface—as well as means for substantially continuously drawing off such gas from the chamber.

The seventh embodiment also includes some means for forming an electrical discharge in the gas between the sample surface and an anode, to form and bombard the surface with ions of the gas and sputter sample atoms out of the surface; and some means for projecting a beam of light through the sputtered atoms and for making measurements of the optical absorbance by the sputtered atoms.

In addition, the seventh embodiment includes some means for automatically controlling the rate of the gas-directing means to optimize such measurements.

Analogously with the sixth embodiment discussed earlier, the seventh embodiment has at least two preferred forms. In one, the apparatus also includes some means for monitoring pressure within the chamber, and the rate-controlling means are responsive to the pressure-monitoring means to maintain the pressure at least approximately constant.

In another preferred form, the rate-controlling means are responsive to the measured values of optical absorbance, to maintain the measurements in an optimum absorbance range.

Now an eighth embodiment of our invention includes solid-sample receiving and supporting means, and also includes variable-rate means for sputtering sample atoms out of the sample surface. This embodiment also includes some means for projecting a beam of light through the sputtered atoms and for making measurements by determining the intensity of the beam after passage through the sputtered atoms.

This eighth embodiment furthermore includes some means for monitoring atomic emission from the sputtered atoms. Finally this embodiment must include some means, responsive to the emission-monitoring means, for optimizing the measurement precision.

As in the two embodiments discussed just previously, there are two preferred forms: in one, the optimizing means automatically control the variable-rate means to maintain constant atomic emission, thereby stabilizing the sputtering rate; in another, the optimizing means provide a signal related to sputtering rate, for use in correcting the measurements for variations in sputtering rate.

A ninth embodiment of our invention is atomic-absorption measurement apparatus for use with a sample. It includes an optical measurement chamber, with windows for passage of a measurement light beam along a light path through the chamber, and some means for generating a stream of sample atoms within the chamber.

This ninth embodiment also includes a baffle disposed within the chamber and along the optical path. The baffle has a multiplicity of holes that are in the optical path, and aligned with the optical path.

The baffle preferably has a "honeycomb" form, and each hole in the baffle preferably has a length-to-diameter ratio of roughly three. Each hole also preferably has a transverse hole dimension of one-eighth inch or less.

Sample atoms in the gas stream are captured on the walls of the baffle and thus prevented from reaching and coating the end windows of the sputtering chamber. By virtue of this capture it is possible to extend very considerably the period of use of the chamber before cleaning is required.

A tenth embodiment of our invention is a method for sputtering atoms from a solid sample for atomic-absorption measurements. The initially exposed surface is assumed to have irregularities or impurities not representative of the bulk sample. The method includes three basic steps.

The first step is to strike a high-energy glow discharge against the initially exposed surface as cathode, and operate the glow discharge for a period of less than one minute to wear away the initially exposed surface and produce a new surface representative of the bulk material.

The second step is to operate a glow discharge at much lower energy against the fresh new surface to produce atoms of the sample for use in atomic-absorption or atomic-fluorescence measurements.

The third step, conducted while operating the glow discharge at the much-lower energy, is to measure the atomic absorption or atomic fluorescence of the atoms produced.

In the first step, we prefer to pulse the high-energy glow discharge, at a rate between approximately ten and approximately twenty hertz inclusive.

As previously mentioned, many of the embodiments that have been described can be combined or superposed in various groupings to form yet other embodiments—i.e., composites. The composites generally possess the combined advantages of the individual embodiments.

All of the foregoing operational principles and advantages of our invention will be more fully appreciated upon consideration of the following detailed description, with reference to the appended drawings, of which:

BRIEF DESCRIPTION OF THE DRAWINGS

FIG. 1 is a perspective or isometric view of apparatus that corresponds to the key module of the first embodiment discussed above. FIG. 1 is partly cut away in a wedge-shaped vertical section to show the interior of the apparatus.

FIG. 2 is in part a longitudinal vertical section (or "sectional elevation") of the FIG. 1 apparatus, and in part a schematic diagram of certain components that make up the context or environment for the FIG. 1 apparatus, and thus complete the first embodiment.

FIG. 15 is a schematic of the flame-burner systems that are generally used for atomic-absorption measurements. FIG. 16 (after D. S. Gough) is a longitudinal section of the previously-mentioned solid-sample sputtering chamber developed at CSIRO, and FIG. 17 (also after Gough) is a greatly enlarged section of the annulus in that CSIRO chamber. FIG. 18 is an even more greatly enlarged section of the region of abutment between the annulus and the sample, during operation.

DETAILED DESCRIPTION OF THE PREFERRED EMBODIMENTS

Figure 3:
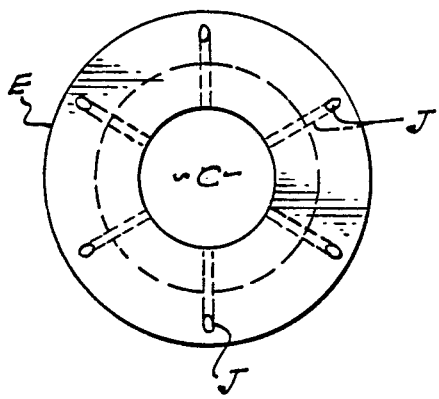
FIG. 3 is a top plan view, partially in broken lines to show hidden features, of an arrestor (or spacer) element that is an important part of the FIG. 2 embodiment.
Figure 4:
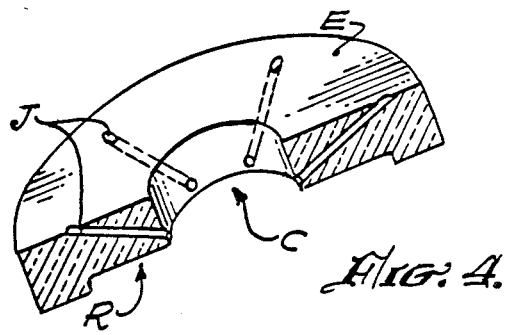
FIG 4. is a perspective or isometric view, shown cut away in section along a diameter, and also partially in broken lines to show hidden features, of the FIG. 3 arrestor (or spacer) element.

The sensitivity of atomic-absorption and atomic-fluorescence analytical techniques is directly related to the population of analyte atoms in view. The first two embodiments of our invention, and preferred forms of them as briefly summarized above, serve to increase both (1) the total number of atoms sputtered and (2) the population of atoms in view, in proportion to total atoms sputtered.

In our apparatus (FIGS. 1 through 14) as in the CSIRO system, gas is introduced into the sputter chamber T close to the surface of the sample P, and drawn away from the sample surface into the measurement path B. The latter is established by a generally conventional hollow-cathode lamp H, monochromator M, and coupling optics L1, L2.

At the same time a glow discharge in the gas sputters sample atoms out of the sample surface and into the gas flowing away from the surface. The gas thus carries with it atoms sputtered from the sample surface.

The chamber T has end windows W1 and W2, a gas inlet GI, a gas outlet GO, an anode A which is shaped to form an annular manifold cavity M, a "cathode" sample abutting surface K and an annular arrestor or spacer E. A sample-access opening may be the aperture in the cathode plate K or the narrower aperture in the anode A. (In a sense the element marked "K" in the drawings may more accurately be denominated a cathode plate, since it charges the sample P so that the sample surface itself serves as cathode.)

In accordance with our invention, as will become clear, this apparatus differs in many geometric and functional details from the CSIRO unit. As a result the geometry of the gas stream is controllable in various ways, and the sputtered atoms too are thereby effectively rendered a controllable stream. This fact is then exploited to optimize the population of atoms in view of the atomic-absorption optical system.

1. ANGLED JET OR JETS

In particular, to form a well-defined gas stream and to confine that stream to a central path well-separated from solid components where atoms would be lost by deposition, we provide a gas jet that is inclined, at a substantial nonzero angle, with respect to the sample surface.

From this jet, an individual small stream of gas impinges directly upon the sample surface at generally the same nonzero angle—and roughly centered in a working aperture of the apparatus. This feature corresponds to the "first embodiment" discussed above.

As shown in FIGS. 1 through 7, an angled jet can direct a high-velocity stream of gas directly against the sample surface. The result is a localized high-pressure zone, a pressure increment, in the region where the individual stream impacts the sample surface. Meanwhile gas ions formed in a glow discharge in the same gas are drawn toward the surface by the potential field of the discharge—the so-called "cathode fall" region.

The glow discharge is concentrated in the high-pressure region, rather than being confined by the arrestor hole. The velocity *added* by the pressure increment has the effect of increasing the amount of sample material atomized.

A further advantage is gained if the structure just in front of the sample surface is configured as a "discharge arrestor," with a shallow annular recess surrounding the ion-bombarded portion of the sample surface. As noted earlier, such a recess is make shorter than the necessary cathode-fall region of the discharge, thereby preventing formation of the discharge within the recess.

This structure is used in a glow-discharge apparatus to keep the active area of the cathode away from the solid components. In an atomic-absorption sputtering chamber, it helps confine the discharge to the inner diameter of the arrestor, thereby minimizing deposition and consequent loss of signal.

Figure 5:
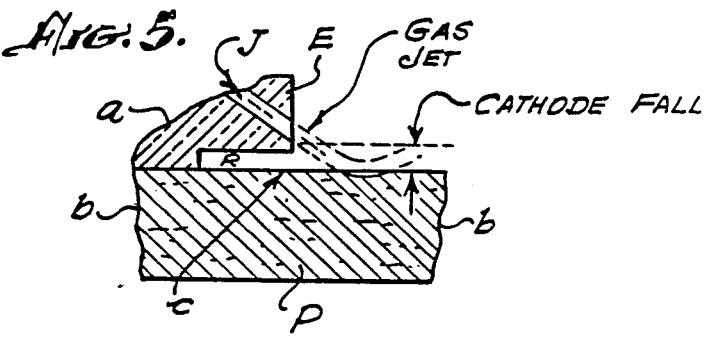
FIG. 5 is a greatly enlarged vertical section, broken away at its periphery, of a detail of the same arrestor (or spacer) as in FIGS. 3 and 4—together with a typical sample, a flow of gas, and additional contextual features.
Figure 18:
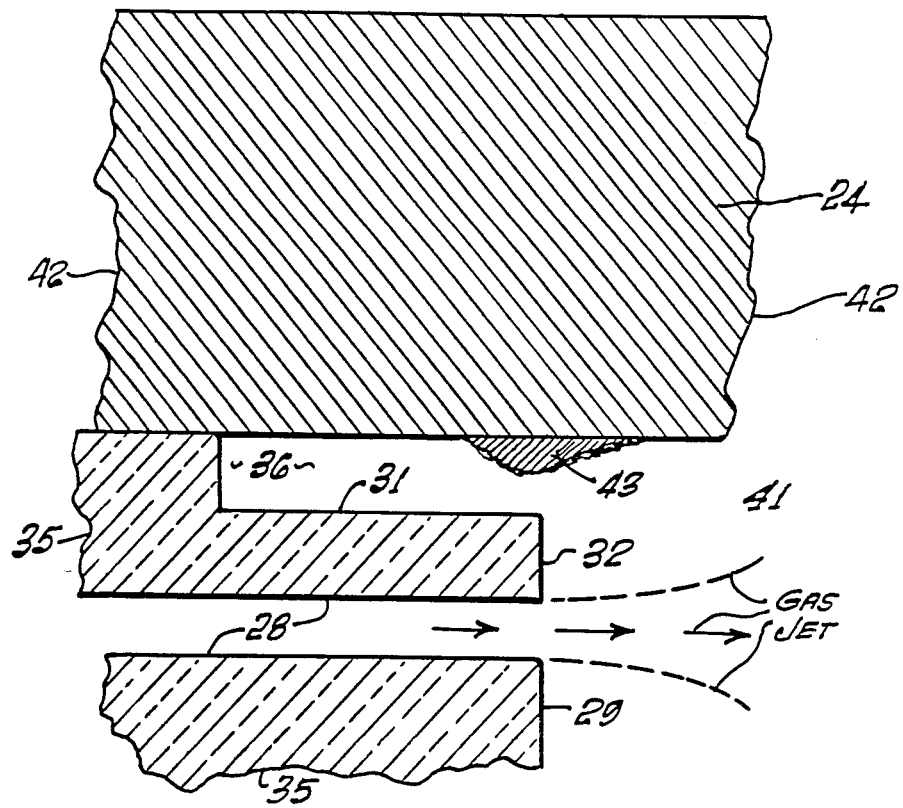

A problem with such arrestors, however, is that sputtered material can accumulate in the mouth of the recess (as shown in FIG. 18) and essentially short out the recess electrically. In our apparatus, as the individual stream of gas from the jet passes the small annular space between the sample and the body of the discharge arrestor, it creates a low-pressure region through a Venturi process. This greatly improves the function of the recess by keeping sputtered material out of the recess itself. An important benefit of this characteristic is longer running time between cleanings, as no significant mound accumulates on the sample surface at c (FIG. 5).

To further enhance the sputtering efficiency and other advantages just described, we prefer to provide not only a single gas jet but an essentially conical array of such jets. From this array, three or more individual small streams of gas impinge directly upon the sample surface at a substantial nonzero cone angle—again, centered in a working aperture of the apparatus.

We believe that the advantages of this conical configuration go beyond preventing accumulation of sputtered material in a discharge-arrestor recess. The centering action of the gas jets can greatly reduce the need for the arrestor. Our invention contemplates elimination of the arrestor-recess function entirely. In the resulting configuration the "arrestor" becomes simply a spacer that separates the anode and (cathodic) sample surface by a suitable distance for support of the discharge—and of course houses the jets.

After impacting the sample surface the individual gas stream from each jet, now carrying the sputtered material, is deflected away from the sample, with a component of motion toward the view path. Of course the individual streams still have a component of motion across the sample surface; however, in our preferred conical-array system, at a small distance from the sample surface the material-carrying streams now collide with each other.

We arrange the jets in a symmetrical array and balance the flows in the individual streams so that in their mutual collision they are deflected in a balanced fashion—that is to say, the gas and sputtered material flow directly away from the sample surface, essentially along a normal to the surface. The combined flow forms a unified stream that is generally centered within the conical array of jets.

This centering action, combined with the high velocity of gas flow compared to the atomic-diffusion rate, helps to minimize loss of atoms due to deposition on the sample and on walls of the sputter chamber. As previously mentioned it also aids in keeping the arrestor recess clear, or may make it unnecessary to provide such a recess at all.

In our apparatus, as illustrated, the anode A is not in the form of a rod across the chamber T from the sample, but rather is a conical annulus just beyond the arrestor/spacer E. In addition, the outer diameter of the anode A is configured to form with the arrestor/spacer E a manifold cavity M that supplies gas to the angled jets J.

If preferred, the jets can be given a "horn" configuration, rather than a simple conical section, and by suitable manifold design their velocity can be controlled so as to enhance other features, which are described below.

Our symmetrical array of angled jets has several advantages: (i) more atoms are sputtered from the sample; (ii) a larger percentage of the sputtered material reaches the absorption path; (iii) the individual gas streams penetrate deeply into the sample, providing a more representative and hence more accurate analysis; (iv) it becomes possible to use a simplified, more economical arrestor/spacer that is more resistant to electrical breakdown but requires low maintenance; and (v) the steams efficiently carry sputtered material away from the sample surface, preventing resputtering and thereby reducing analytical errors due to diffusion-rate variations among the elements.

2. AXIAL VIEWING AND RELATED FEATURES

The atom population generated by the sputtering process contains atoms in several elevated atomic states as well as the ground state. Only the ground-state atoms will absorb the resonant radiation emitted from the light source and, by virtue of that absorption, be quantitatively sensed by the monochromator and detector.

Significant quantities of these single ground-state atoms may be lost to the detection system by two principal processes: they may collide with the walls of the discharge chamber and adhere; and they may travel a path out of view of the light passing through the chamber. The second embodiment of our invention minimizes these two loss mechanisms, as explained below.

(a) Axial viewing—One way to increase the number of atoms in view is to bend the stream of atoms emitted from the sample in such a manner that the measurement light beam passes through a greater population of atoms.

Figure 6:
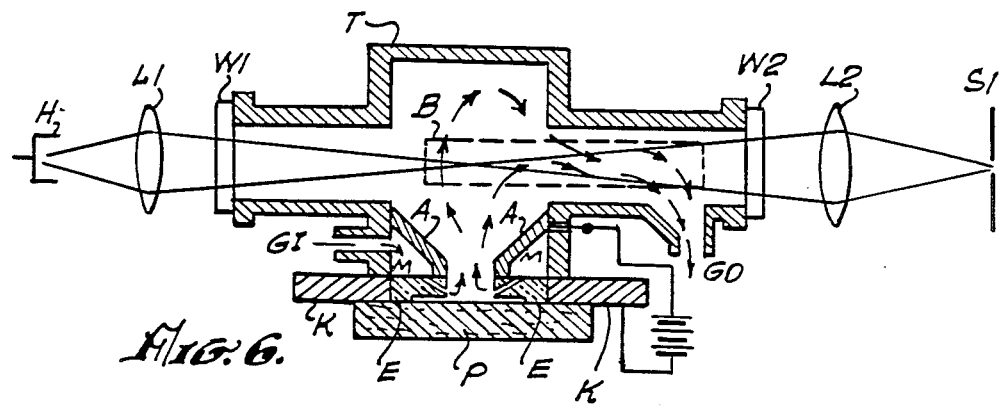
FIG. 6 is a longitudinal vertical section and diagram, similar to FIG. 2, of apparatus corresponding to the second embodiment discussed above.

To accomplish this, as shown in FIG. 6, the exhaust port GO is placed on the same side of the chamber as the sample P, forcing the emitted atoms to follow a long path, generally coincident with the optical path. The "line of sight" of the measurement optics now intercepts a greater number of atoms than if the exhaust port were directly across the chamber.

(b) Contoured deflector—The natural diffusion process tends to dissipate the atoms quickly upon ejection from the sample surface. This undesirable effect is increased by turbulence.

In order to reduce turbulence and thus increase the number of atoms delivered to the viewing region we provide a curved-surface atom deflector which quickly directs the atom stream into the absorption path. It also concentrates more atoms in the center of the light beam.

Figure 7:
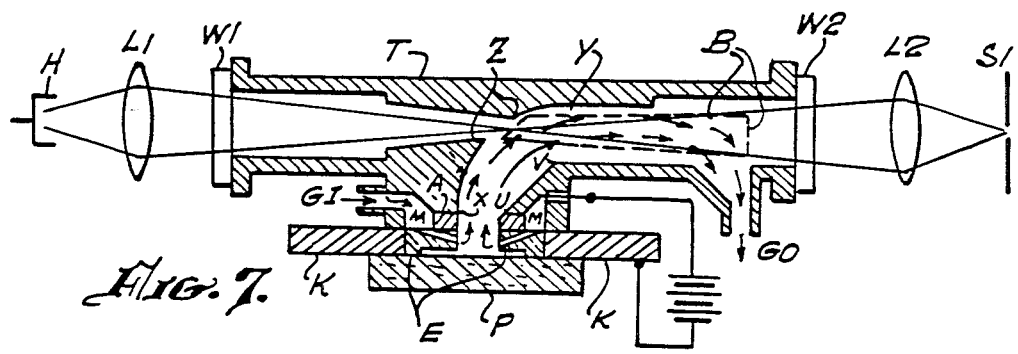
FIG. 7 is a view similar to that of FIG. 6, but showing a preferred form or variant of the second embodiment—namely, one in which a solid, contoured deflector is provided for the gas stream.
Figure 8:
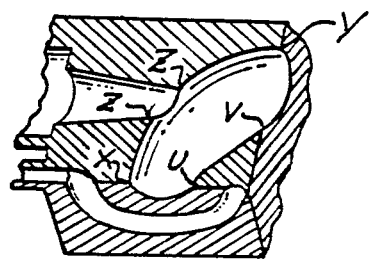
FIG. 8 is a perspective or isometric "two-way section" of the gas-stream guide portion of the FIG. 7 embodiment, one facet representing a vertical longitudinal section along the centerline of the apparatus, and another facet representing a vertical cross-section just "downstream" from the sample aperture. This view is taken from below, and consequently also shows part of the contouring of the underside of the guide portion.

As shown in FIG. 7 and 8, the inner surface of the deflector is essentially a ninety-degree section of a toroid, from the entry port A-U to the measurement section V-Y. (FIG. 8 may be slightly confusing until one recognizes that it shows the internal, concave surfaces of the deflecting cavity and communicating chambers.) The deflector is made of metal or other suitable solid material, and partway around it there is a relatively small aperture Z—Z for entry of the light beam.

The contoured deflector is of particular importance when the atom stream is being bent to obtain axial viewing.

Figure 9:
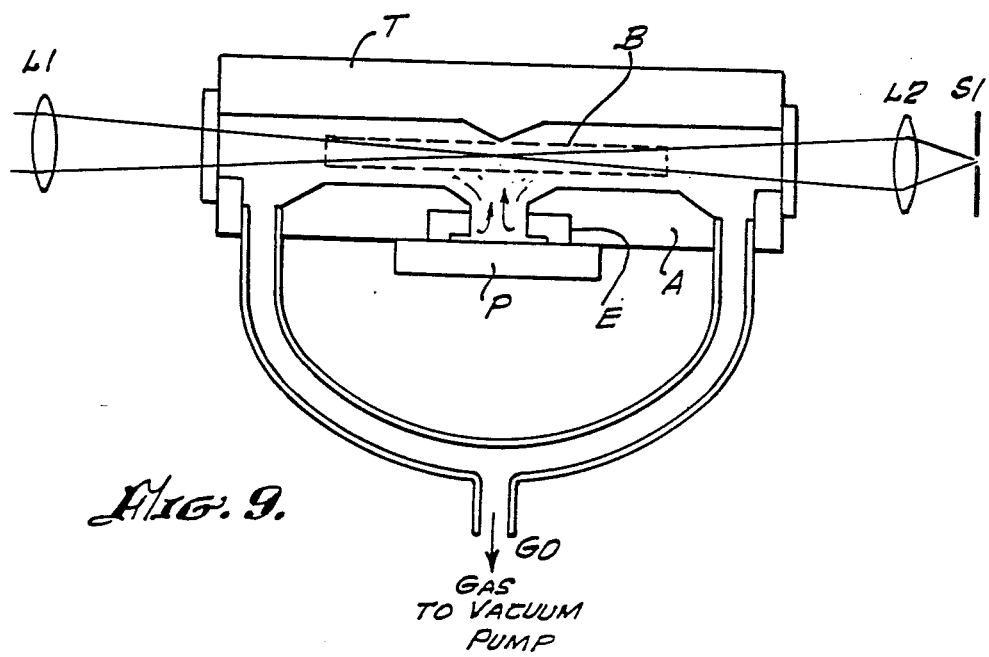
FIG. 9 is a longitudinal vertical section and diagram, similar to FIGS. 2 and 6, of apparatus corresponding to another preferred form or variant of the second embodiment—namely, one in which the gas stream is split to form a double-length volume of sample atoms, with viewing along the entire double length.

(c) Dual pumping—Another feature that can increase the atom population in the absorption path is diversion of the atoms sputtered from the sample into two streams moving in opposite directions. The two streams are effectively aligned so that the optical path traverses both streams in sequence. FIG. 9 shows one arrangement for doing this: a pumping manifold provides substantially equal pumping at both ends of the sputter chamber.

Such dual pumping has four principal advantages: (i) increased absorption pathlength; (ii) in retrofits for existing AA spectrometers, location of the densest part of the atom cloud at a common image point of both the hollow-cathode lamp and the monochromator entrance slit; (iii) minimum "insertion loss" for the sputter chamber, and hence maintenance of optimum signal-to-noise ratio and measurement precision; and (iv) lower pump-down time, and hence lower overall analysis time.

3. DISCHARGE CURRENT ADJUSTMENT TO LINEARIZE ABSORBANCE

As previously mentioned, one of the major handicaps of the atomic-absorption method has been poor dynamic range. Our invention provides for an increase in dynamic range from one or two orders of magnitude—hitherto common in atomic-absorption work—to five orders of magnitude, in analysis of a solid sample.

Our invention accomplishes this increase in dynamic range by addressing the problem of nonlinearity of calibration curves that relate absorbance to analyte concentration.

The concentration of atoms delivered to the measurement path by sputtering form a glow discharge is proportional to the electrical current flow in the discharge. By controlling the current, one can therefore regulate the ratio of (1) atoms delivered to (2) atom concentration in the solid sample.

Thus if the concentration in the sample is very high the current may be reduced to provide some desired atom concentration in the view path, and conversely. Such "desired" concentration is that which permits measurement of absorbance in the linear portion of the calibration curve.

Thus our invention increases dynamic range in atomic-absorption analysis by providing for discharge-current adjustment to proper levels. Adjustments may be performed manually or automatically—for example, under computer control—in response to the instantaneous measured absorbance going out of range. Accompanying each stepwise change in discharge current is a corresponding shift in displayed or recorded calibration range.

Figure 10:
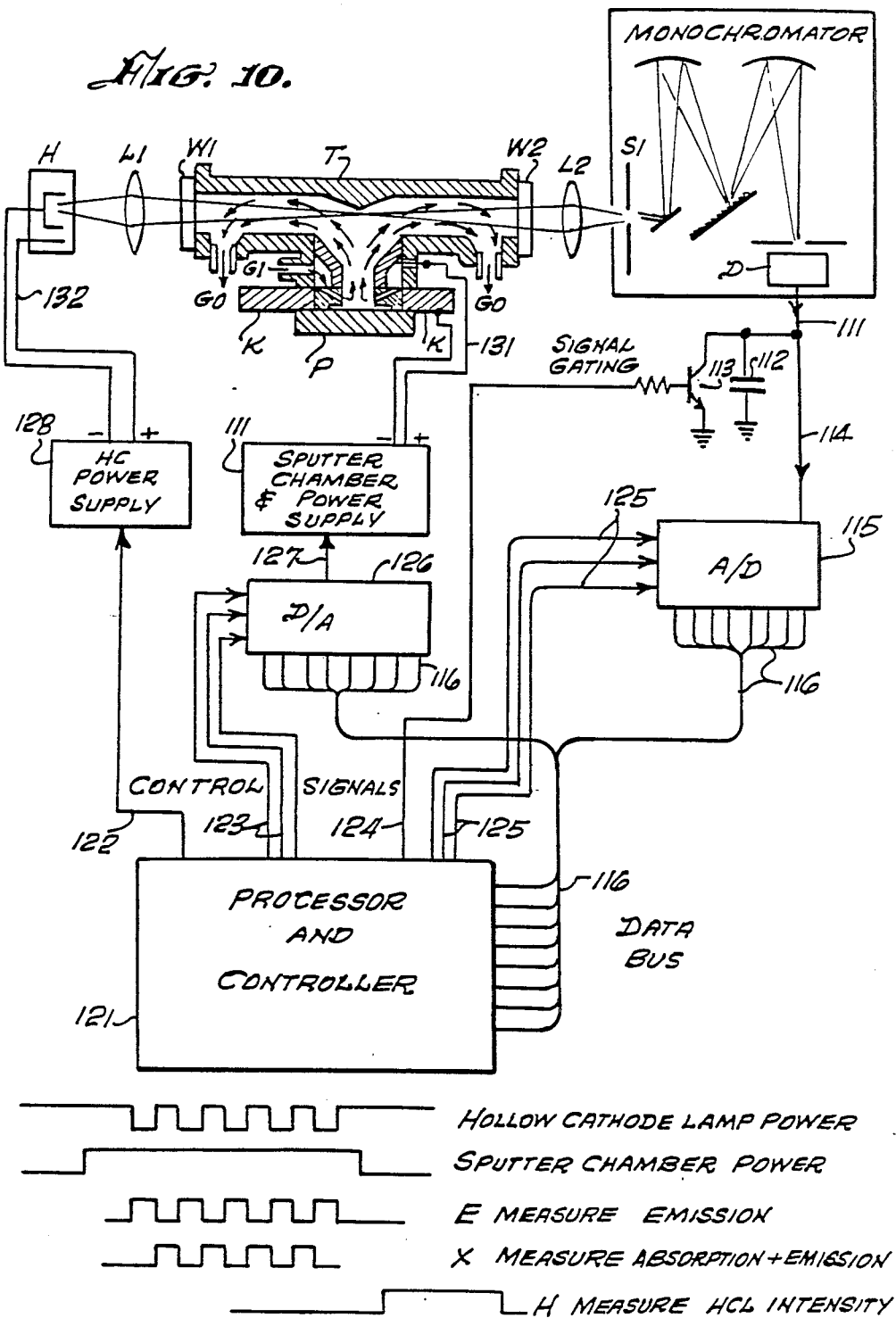
FIG. 10 includes a view similar to FIG. 9, along with a highly schematic representation of optical and electronic components corresponding to the third or fourth embodiment discussed above (those in which discharge current is adjusted to bring the absorbance signal into the linear region of the absorbance curve, or to hold the absorbance signal constant).
Figure 11:
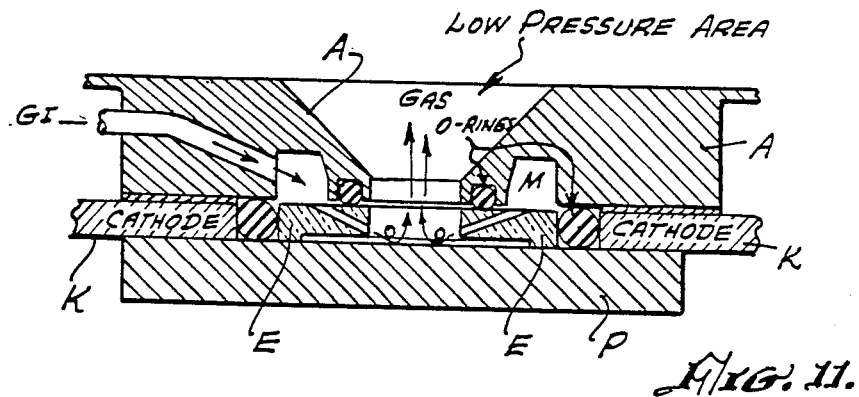
FIG. 11 is a longitudinal vertical section of the central portions of apparatus corresponding to the fifth embodiment (in which a resilient member between the anode and spacer accommodates tolerances, so that both the cathode and the spacer closely contact the sample).

FIG. 10 illustrates a system in which discharge current can be adjusted to one of several levels, each associated with a particular calibration curve that covers a corresponding limited concentration range.

As will be plain to those skilled in the art of modern digital electronics, the electronic portions of the illustrated apparatus constitute a generalized system which can be programmed for operation in any one of a great variety of ways. It is by virtue of this generality that this same schematic is used in connection with other embodiments of our invention as presented below. Among such operational modes is merely semiautomatic operation, in which key parameters are displayed and the system awaits manually entered commands.

Our own preferred operational sequence will be described shortly, following an overview of the hardware. The sampling and optical equipment, as can be seen, are as already described above—from the hollow-cathode lamp H, entrance lens L1 and window W1, through the glow-discharge sputtering chamber T, and out through the exit window W2 and lens L2 to the monochromator S1-S2 and detector D.

An output signal 111 from the detector is filtered by a capacitor 112, and unless shorted to ground by the signal-gating switch 113 proceeds as at 114 to an A/D ("analog-to-digital") converter 115. Sequencing and other operational details of the A/D converter 115 are managed by, e.g., three control lines 125. The output of the A/D converter appears on a group of, e.g., eight data lines as a digital representation of the light-beam intensity at the detector.

Another interface point between the digital electronics and the sampling equipment involves the supply of power to the glow discharge. Discharge power is applied between the anode A and cathode plate K by electrical leads 131, from a variable power supply 111. This adjustable power supply 111 is adjusted by an analog control signal 127 received from a D/A ("digital-to-analog") converter 126.

The characteristics of the analog control signal 127 are in turn derived from digital inputs appearing at, e.g., eight data lines 116 entering the D/A converter 126; while sequencing and other operational details of the D/A converter 126 are managed by, e.g., three control lines 123. The digital-input lines effectively carry a digital representation of the desired current, voltage or power in the glow discharge.

Other arrangements for adjustment of the supply power at 131 will occur to those skilled in the electronic arts.

A similar supply-voltage system is illustrated in abbreviated form for the hollow-cathode lamp H. The lamp receives power on leads 132 from a power supply 128, which is shown as controlled by a single control line 122. In systems requiring no variation of lamp intensity, such a single control line 122 may suffice, to simply turn the lamp on and off as required by an operational plan. The control system 116-123-126-127 shown for the sputtering-chamber power supply is of course applicable for other voltage-supply applications.

At the heart of the electronics system is a processor and controller unit 121, which receives detector data from the A/D converter 115—and sends power-supply-control data to the D/A converter 126—on a data bus 116. The processor-controller 121 also provides operational management signals to the converters 115 and 126 on control lines 125 and 123, respectively. In addition, the processor-controller 121 controls the hollow-cathode-lamp power supply 128, and the signal gate 113 by control signal 124, by suitable signals 122.

Preferred timing cycles for operation of the various system functions are sketched at the bottom of FIG. 10. As indicated, the lamp power can be electrically chopped to provide modulation of the atomic-absorption signal.

Power to the sputtering-chamber glow discharge is preferably chopped on a longer cycle to establish an essentially steady-state supply of atoms in the absorption measurement path. "Off" intervals of the glow discharge are useful, however, for measurement of the hollow-cathode-lamp intensity as indicated by the bottom sketch. (As will be understood, such data permit lamp-drift corrections.)

As illustrated, atomic emission can be best measured during the "off" intervals of the lamp H, to avoid confusion of atomic emission with light from the lamp. (This timing may be desirable even if emission is measured at right angles as in FIG. 14, to avoid interference by scattered light from the lamp.) Emission and absorption can be measured together during the "on" intervals of the lamp, and if desirable the emission value found while the lamp is off can be used to correct the absorption measurements for the effects of emission.

Now as to use of this system for automatic measurement-range control: suppose that the concentration of the sample for the element in question is completely unknown. The current or "excitation" is adjusted to the lowest preset level, which corresponds to the highest concentration range of the instrument. A quick measurement indicates whether the concentration of the element in the sample provides an absorbance value within the optimum working range for this excitation level.

If the absorbance is too high, the sample concentration may be essentially out of range of the instrument. If the absorbance is too low, the current is increased and another quick determination made to check absorbance level. In this way a range is found that allows measurement in the linear part of the absorbance scale, if such a range exists for the sample at hand.

An operator can perform this procedure manually, by pressing an "up" key for increasing current or a "down" key for decreasing current. In a system with data interconnection the process can be automatic.

4. DISCHARGE-CURRENT SERVOCONTROL TO OPTIMIZE ABSORBANCE

Precision of atomic-absorption analysis, in terms of composition of the analyte, depends in part on the slope of the calibration curve that relates absorbance to concentration. A high change in absorbance per unit change in concentration yields a higher precision (or at least sensitivity) than the reverse. Such calibration curves are usually nonlinear, bending to unfavorable slopes at higher concentrations.

Our invention contemplates automatic driving of the discharge current so that the concentration of atoms in the view path provides the most desirable absorbance from a measurement standpoint. The current required to reach this point is then measured—and presented in terms of percent concentration of the analyte.

In addition to thus providing automatically an analytical measurement at the most precise point of the calibration curve, regardless of concentration, this embodiment of our invention provides for automatic expansion of dynamic range as necessitated by the concentration of the analyte in the sample. In effect the principle of the third embodiment of our invention is here carried one step further.

Referring again to FIG. 10, the processor and controller 121 computes absorbance as $(X-E)/H$, where $X$ represents measured absorbance with emission superimposed, $E$ represents emission alone, and $H$ represents the hollow-cathode-lamp intensity as measured alone. The processor/controller then computes the difference between the target absorbance and measured absorbance.

This difference is put through a digital filter (within the processor and controller 121) and into the D/A (digital-to-analog) converter 126, whose output at 127 controls the sputtering-chamber power supply 111. A typical filter for a simple log network is $Y = K(X − P) + P$, where Y is the new output to the D/A 126 and P the previous value. X-P is the difference between the target absorbance and the measured absorbance.

K has a small value between 0.1 and 0.001, depending on the computing rate, or specifically the absorbance measurement and computation time. The target absorbance value is a fixed value chosen for the greatest precision in the determination of concentration, and the concentration itself is derived from the sputtering-chamber drive current or power—e.g., the discharge current 131.

Initially the system selects a low value for the sputtering-chamber drive current 131, corresponding to 100% concentration of the element to be determined. The system starts computing the difference in actual absorbance from the target value. The difference is processed via the digital filter to generate a series of new sputtering-chamber drive currents 131 which would increase at the start until the actual value equals the target value.

The final value of the drive current 131 is used to calculate concentration of the element to be analyzed. This calculation utilizes an equation developed from a selection of metal standards. The constants for the equation are stored within the system. Generally a low and high value are used periodically to trim the equation, to account for progressive changes in the condition of the equipment.

If the concentration of the element falls to trace levels, the sputtering-chamber drive current increases to a maximum limit but the absorbance still fails to reach the target value. In this case the concentration is computed on the basis of the absorbance level achieved at this highest drive current, with an optional out-of-range indication.

5. FRONTAL COOLING, WITH RESILIENT MOUNT FOR ARRESTOR/SPACER

During the atomization (sputtering) process, heat is generated at the sample surface in proportion to the power in the electrical discharge. Unless heat is carried away rapidly, the sample and adjacent parts of the apparatus overheat, degrading the accuracy of the analysis.

Furthermore, to maintain a constant sputtering rate and thus precise absorbance readings, the sample temperature should be held constant. Accordingly it is necessary to cool the sample to a stable temperature.

In accordance with our invention the sample is cooled at its frontal surface by a water-cooled cathode plate K (FIG. 11) that surrounds and firmly engages the bombarded, active part of that surface. Pressure between the cathode plate and the sample should be in the range of twenty to fifty pounds per square inch, for adequate and consistent cooling.

Not only sample-temperature stabilization, but operation of the sample at cathode potential as well, requires close contact between the sample P and the cathode plate K. Reliable operation at cathode potential can contribute both to measurement precision and to safety. As to the latter, we prefer to run our cathode at ground potential, and in this case holding the sample P reliably at that same potential protects the operator against electrical shock.

For these reasons the cathode plate K should make firm contact with the sample P. For good measurement precision the arrestor/spacer E too should make firm contact with the sample P.. If the arrestor/spacer E is in fact an arrestor—i.e., a spacer with a discharge-inhibiting recess, as in FIG. 11—firm contact is doubly important since it helps to maintain the proper depth of the recess. This condition is necessary to prevent high voltage and sputtering in the recess.

Normal production tolerances on the assembly, however, would not permit all three parts (sample surface, cathode plate and arrestor/spacer) to be adequately coplanar. We therefore provide a "floating" resilient mounting for the arrestor/spacer E. This mounting presses the arrestor/spacer firmly against the sample, while permitting the sample to come in contact with the water-cooled cathode plate K upon application of modest pressure to the sample. By virtue of this added degree of freedom in the assembly, the sample surface firmly engages both the arrestor/spacer and the water-cooled cathode plate.

A practical and inexpensive way to obtain these several advantages is to use an O-ring (see FIG. 11) as the resilient mounting. The O-ring provides 0.002 to 0.003 inch "float" for the arrestor, ensuring that the cathode plate and the arrestor can both contact the sample simultaneously.

6. VARIABLE PUMPING

Precision in absorbance measurements requires stabilizing the rate of disassociation (sputtering) of sample. The sputtering rate in turn is determined by several factors. Consequently it is desirable to control as many of these factors as possible.

One such factor is pressure of the gas in the sputter chamber. Pressure is usually brought to the 5-to-20-torr range by means of a vacuum pump.

In other uses of a controlled sputter chamber (that is, other than atomic absorption), pressure is customarily controlled by manual adjustment of a needle valve—admitting gas in varying amounts to adjust the pressure to a desired value.

Our invention contemplates control of pressure independently of flow rate, through control of the vacuum-pump pumping rate. In addition to its effect on sputtering stability, changing the pumping rate is an alternative way to change the sputtering rate to extend dynamic range.

Figure 12:
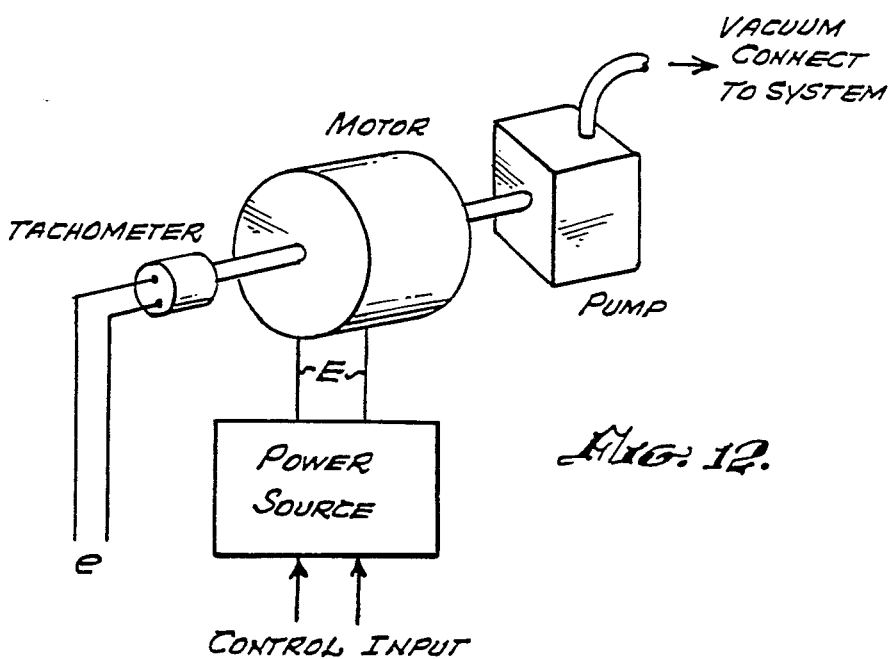
FIG. 12 is a generally schematic representation of certain components used in the sixth embodiment (that in which gas pumping is automatically controlled to provide constant pressure or optimum absorbance).

In one preferred form of this embodiment of our invention, pumping rate is varied by controlling the rotational speed of the pump driveshaft. FIG. 12 shows one system for accomplishing this: a power source provides voltage E for operation of an electrical motor, which drives the pump. The motor also drives a tachometer, which provides a voltage e proportional to rotational speed. This voltage can be used to monitor the rate of rotation.

In an automatic configuration the control system provides a control input signal of sufficient magnitude to bring the tachometer output e to a target value which corresponds to the desired pumping speed.

Either a dc or an ac motor may be employed. If the motor is a dc unit, the power source provides current amplification for the control-signal input. (In simple terms, a triac or SCR may be effectively wired to regulate the electrical motor that drives the vacuum pump.) If a synchronous ac motor is used, the power source instead provides an ac output whose frequency is responsive to the control-signal input.

In either event an electrical feedback circuit is employed to control the power source from the tachometer output e.

In another preferred form of this embodiment of our invention we install a combination of three or more solenoid valves in parallel with each other but in series with the vacuum line between the pump and the sputter chamber. The solenoids are controlled by a microprocessor in binary fashion: for example, using three solenoid valves with different apertures seven different pumping rates (and zero) can be obtained.

7. VARIABLE GAS SUPPLY

Figure 13:
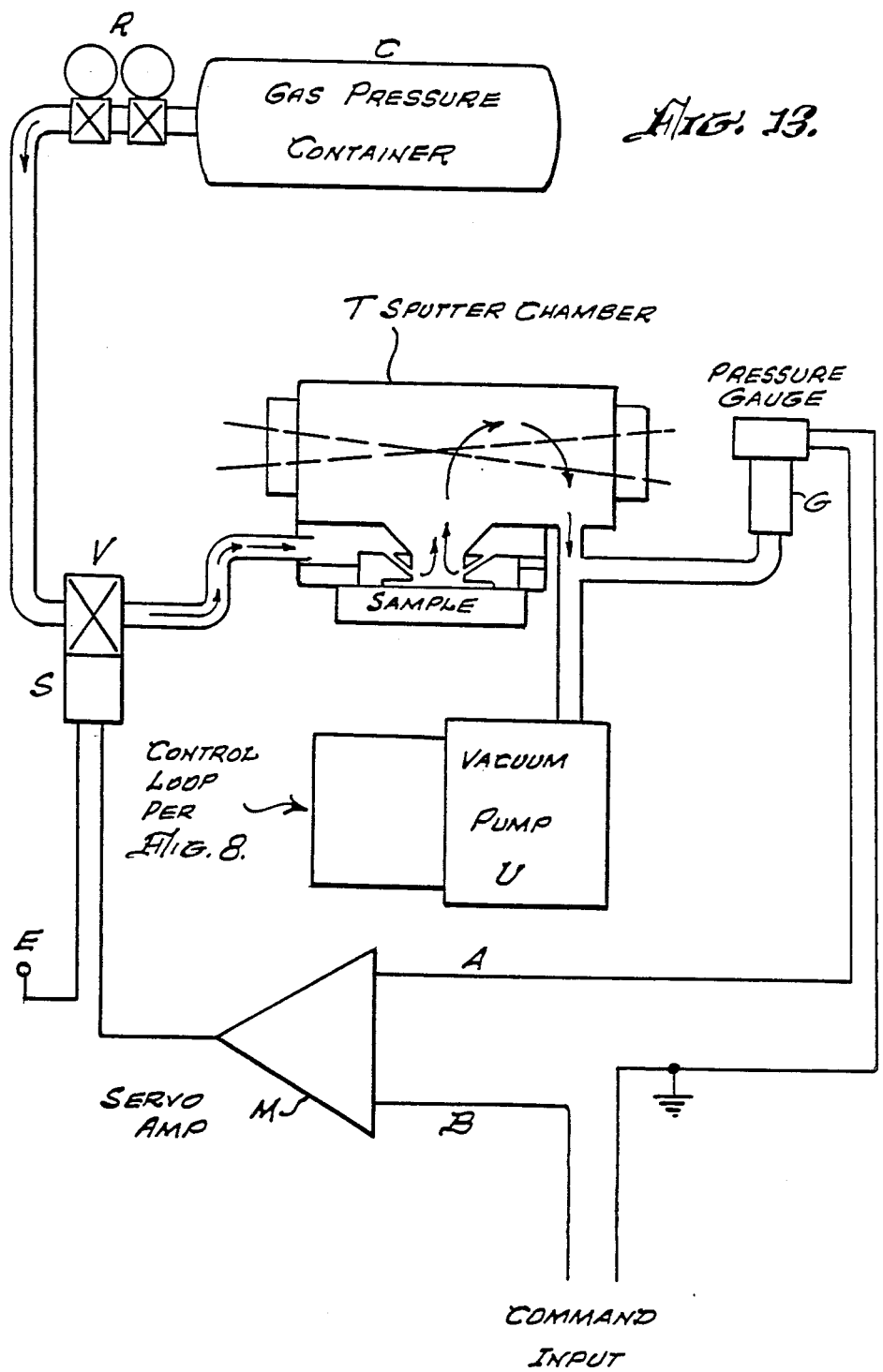
FIG. 13 is a schematic representation of a system that encompasses both the sixth and seventh embodiments. (In the seventh, gas-supply rate is automatically regulated to stabilize pressure or maintain measurements in an optimum absorbance range).

As stated in the preceding section, gas pressure can also be controlled by control of pumping rate. In addition it is desirable to control gas pressure by controlling the amount of gas admitted to the sputtering chamber—i.e., the flow rate. This may be accomplished by means of a closed-loop circuit incorporating a pressure sensor, as shown in FIG. 13. (Previously gas flow has been adjusted by means of a needle valve.)

Pressure in the sputtering chamber T depends in part on the amount of gas mass flow through a valve V controlled by a solenoid S. The valve V is fed from a regulator R, which in turn is attached to a gas container C. The vacuum pump U provides a constant pressure at a fixed volume. If the gas mass flow is increased by opening the valve V, the pressure must rise to handle increased mass at the fixed volume.

A pressure gauge G in communication with the chamber T provides an output signal A, representative of the pressure in the chamber, to one input terminal of a servoamplifier M'. If a command signal B is introduced at the second input terminal, the amplifier generates a servocontrol signal which adjusts the valve V by means of the solenoid S.

This feedback system can continuously trim the valve, and thereby the flow rate, to bring the pressure in the chamber T to a target value and hold it there as long as desired.

The target value is established as a set point by the command signal B. A microprocessor (not shown) provides this set level by supplying a numerical value to a digital-to-analog converter (not shown) which feeds an analog signal into a sample-and-hold circuit.

The output of the sample-and-hold circuit is connected to the reference input B of the servoamplifier. If desired, the microprocessor can also read the pressure by multiplexing the pressure-gauge output through an analog-to-digital converter, and comparing the value read to a stored curve. Such an arrangement allows the microprocessor to monitor pressure for several purposes.

Alternatively the solenoid S and valve V can be controlled in response to a flowmeter, to hold the flow rate at a desired level—while chamber pressure is controlled at the pump as described earlier.

Our invention contemplates controlling gas pressure automatically to maintain both current and voltage at desired levels. Such gas-pressure control may be achieved by use of the embodiments presented in sections 6 and 7 of this Detailed Description either separately or in combination, or by other apparatus.

By controlling gas pressure automatically while maintaining both current and voltage at desired levels, our invention also improves control of the sputtering process.

8. EMISSION MONITORING TO OPTIMIZE PRECISION

Although atomic-absorption analysis deals primarily with ground-state atoms, there is atomic emission arising out of the sputtering process as ionized atoms drop to lower levels. This emission emanating from the discharge varies with sputtering rate, and so may be used to monitor—and control or compensate for—the sputtering rate. In these ways the measured atomic absorption can be normalized with respect to sputtering rate.

The most direct relationship and best control would derive from monitoring the intensity of a single spectral line of the matrix element—for example, iron in a sample of steel. Useful control has been observed, however, with monitoring of atomic emission across the ultraviolet region, in which there are many spectral lines of the matrix element.

Figure 14:
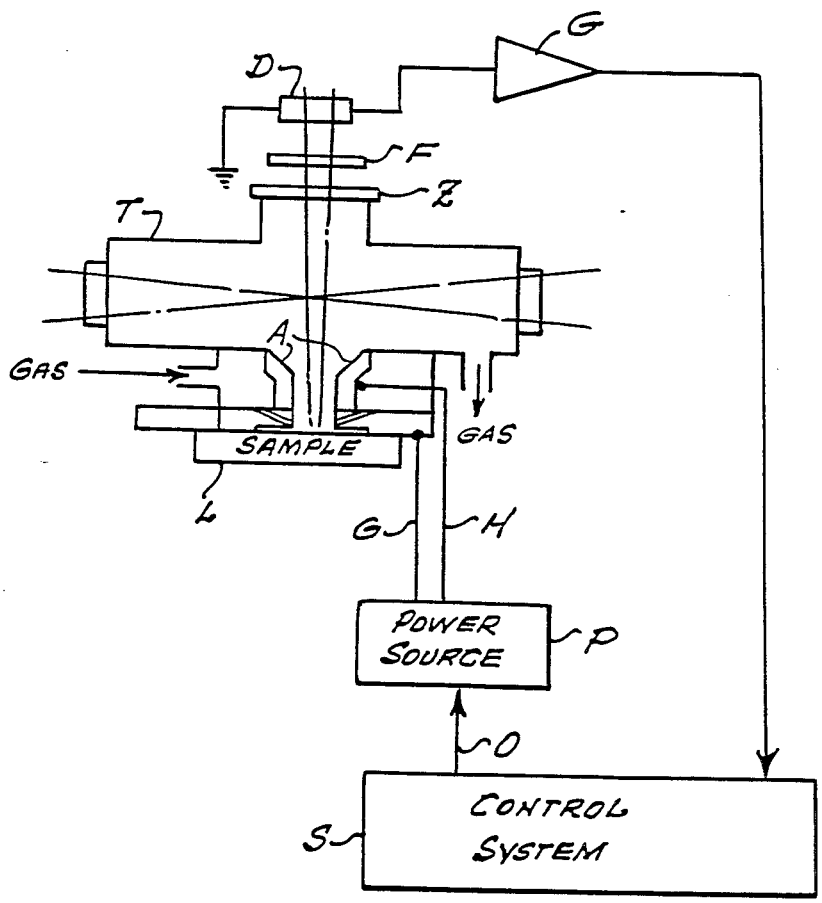
FIG. 14 is a schematic representation of a system tht corresponds to the eighth embodiment (use of an emission signal to physically or arithmetically normalize the absorbance measurements).
Figure 15:
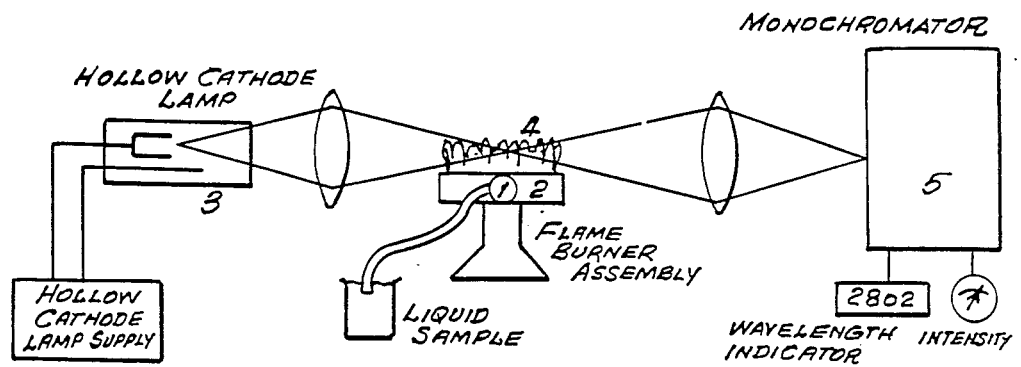
FIG. 15 through 18, already discussed in detail, represent prior-art systems.
Figure 16:
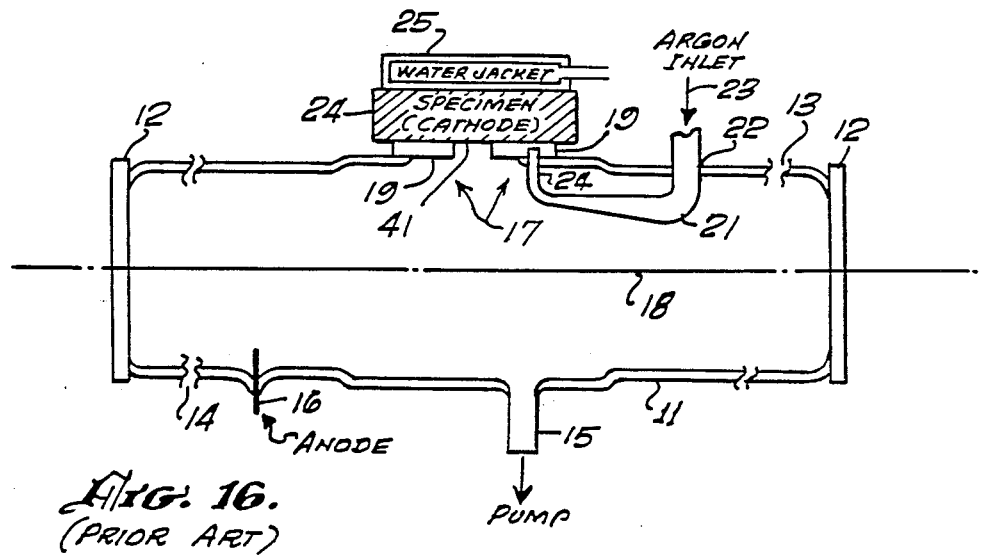
Figure 17:
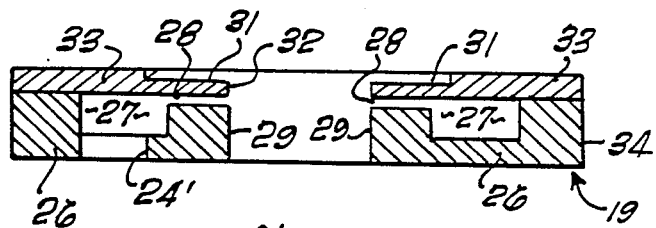

FIG. 14 depicts a control system for stabilizing the absorption measurement by monitoring a portion or all of the emission. The atomic-emission radiation from the discharge passes through the sputtering chamber T and through a diametrically opposite window Z and associated filter F to strike an auxiliary detector D.

The signal from this detector is amplified in an amplifier G for feedback to the control system S. If the signal from the amplifier G indicates decreasing emission, the control-system output O changes to increase the voltage or current from the power source P; and conversely.

In this way the emission is held to as desired value, and correspondingly the sputtering level is set to a predetermined value. A single feedback loop thus compensates for a multitude of factors that influence the sputtering level.

Alternatively, as noted above, the atomic-emission signal from the amplifier G can be used as a basis for standardization calculations (at their simplest, a simple division step) to correct the absorbance readings.

We have discussed the desirability of controlling various parameters—including pressure, flow rate, and glow-discharge current—that affect the sputtering rate. In particular, through pressure adjustment it becomes possible to control discharge current and voltage independently; or even to maintain constant power.

In any of these methods either the voltage or current in the discharge can change, depending on which parameter is controlled. In the case of constant power, for example, the voltage can rise and thereby force a decrease in current.

9. WINDOW-PROTECTIVE BAFFLE

Atoms moving along the optical-system axis of the sputtering chamber tend to coat the end windows, adding to the background absorption both variably and progresively during the course of the measurement. Such background changes degrade measurement accuracy—particularly for high-discharge-current operation, in which the atoms can form a very substantial coating on the windows.

A piece of honeycomb material can serve as a baffle to capture the bulk of the material while allowing passage of the measurement light beam, and so to avoid measurement degradation. The atoms adhere to the baffle walls by natural lateral diffusion, and therefore do not reach the windows.

The baffle holes are aligned with the optical path. The individual cells preferably have length-to-diameter ratio of approximately three to one, and diameter of one-eighth inch or less. The wall thickness too should be kept to a minimum, to minimize loss of signal by simple blocking of the beam.

10. HIGH-ENERGY PRESPUTTERING

As mentioned earlier in the discussion of the background of this invention, extremely protracted presputtering has been required to clear away surface peculiarities of the particular specimen. In this way previous workers have brought observed readings to an "equilibrium" characteristic of representative bulk material before taking what were considered the actual measurements. Unfortunately the presputtering time has been so long as to render the overall analysis time prohibitive.

In accordance with our invention, a better method is to presputter the sample surface at high energy—i.e., using high voltage and/or high current in the glow discharge—to remove an entire layer of surface material much more quickly, but in a highly controlled way. This highly energetic presputtering may use either pulsed or dc current in the discharge.

We have found experimentally that high-current pulses at ten to twenty hertz produce equilibrium in seconds rather than minutes.

It will be understood that the foregoing disclosure is intended to be merely exemplary, and not to limit the scope of the invention—which is to be determined by reference to the appended claims.

We claim:

1. Apparatus for sputtering atoms from a sample surface of a solid sample for atomic-absorption or -fluorescence measurements, said apparatus being for use with a supply of gas; and said apparatus comprising:
   means defining a chamber for containing the gas, said chamber having an internal surface;
   means for receiving and supporting the solid sample, said receiving and supporting means defining a sample-access opening that communicates with said chamber;
   means for supplying a stream of the gas and for directing the stream toward said opening from said chamber internal surface;
   the supplying and directing means comprising at least three jets arranged about said chamber internal surface in a substantially conical array, said conical array having a cone vertex angle substantially less than one hundred eighty degrees, to direct the gas in at least three substreams meeting substantially centrally at said sample-access opening;
   means for drawing the stream of gas away from the sample surface, within the chamber said substreams deflected each other to form
   the gas stream flowing away from the sample surface;
   means, including an anode positioned and arranged with respect to the chamber, for forming an electrical discharge, in the gas that is between said sample-access opening and said anode, to sputter the atoms out of the sample surface for motion with the gas stream flowing away from the sample surface;
   whereby the atoms and the gas stream flowing away from the sample surface tend to be concentrated in a region, within the chamber, that is spaced away from said opening, and from said receiving and supporting means, said supplying and directing means, and said anode;
   whereby said region is an approximately columnar volume defined within said conical array of jets and radially spaced inwardly therefrom, but extends axially past said array of jets;
   means for projecting a beam of light through the gas stream flowing away from the sample surface; and
   means for detecting intensity of said beam after passage through the gas stream flowing away from the sample surface.

2. The apparatus of claim 1, wherein:
   said jets are substantially symmetrically disposed so that the substreams deflect each other along very generally the axis of said array to orient the gas stream flowing away from the sample surface very generally along said axis;
   whereby said region, in which the atoms and the gas stream flowing away from the sample surface tend to be concentrated, is defined along very generally said axis of said conical array of jets and distinctly spaced radially inwardly from said jets, but extends axially past them.

3. Apparatus for sputtering atoms from a sample surface of a solid sample for atomic-absorption or -fluorescence measurements, said apparatus being for use with a supply of gas; and said apparatus comprising:
   means defining a chamber for containing the gas;
   means for receiving and supporting the solid sample, said receiving and supporting means defining a sample-access opening that communicates with the chamber;
   at least three jets, arranged within the chamber in a substantially conical array, said conical array having a cone vertex angle that is substantially less than one hundred eighty degrees, to direct the gas in at least three substreams meeting approximately centrally at said sample-access opening;
   whereby the substreams deflect each other to form a gas stream flowing away from the sample surface;
   means for drawing the stream of gas away from the sample surface, within the chamber;
   means, including an anode positioned and arranged with respect to the chamber, for forming an electrical discharge, in the gas that is between said sample-access opening and said anode, to sputter the atoms out of the sample surface for motion with the gas stream flowing away from the sample surface;
   means for projecting a beam of light through the gas stream flowing away from the sample surface; and
   means for detecting intensity of said beam after passage through the gas stream flowing away from the sample surface.

4. The apparatus of claim 3, wherein:
   said receiving and supporting means define a sample-receiving plane; and
   said chamber-defining means further comprise a discharge arrestor within said sample-access opening for disposition at said sample-receiving plane; and defining an aperture for passage of the gas stream flowing away from the sample surface;
   whereby the atoms and the gas stream flowing away from the sample surface tend to undergo effective concentration in a region that is spaced away from said sample-access opening, and from said receiving and supporting means, and from said jets, and from said anode;
   wherein said effective concentration of the atoms and the gas stream tend to deter shorting of said arrestor.

5. The apparatus of claim 4, wherein:
   the substreams mutually deflect each other approximately along the axis of said conical array to confine the gas stream flowing away from the sample surface and said electrical discharge therein to a region approximately along said axis;

whereby no annular recess is needed in said arrestor aperture.

6. The apparatus of claim 4, wherein:
said arrestor aperture is substantially circular and has two sections of different diameters;
one of said sections is positioned substantially at said sample-receiving plane, for contact with the sample surface, and has the larger of said two diameters; and
the other of said sections is spaced axially from the sample-receiving plane, by a distance that is much smaller than the minimum dark-space length of a glow discharge to
form with the sample surface an annular recess in which no glow discharge can exist.

7. The apparatus of claim 6, wherein:
said jets are substantially symmetrically disposed; and
the substreams mutually deflect each other approximately along the axis of said conical array to confine the gas stream flowing away from the sample surface, and said electrical discharge in the gas stream, to a region approximately along said axis;
whereby the mutually deflected symmetrical substreams minimize sputtering of the atoms into said annular recess and thereby deter blocking of said annular recess by the atoms sputtered from the sample surface; and
whereby the mutually deflected symmetrical substreams help to minimize loss of atoms by deposition on said apparatus.

8. Apparatus for sputtering atoms from a sample surface of a solid sample, for atomic-absorption or -fluorescence measurements, said apparatus being for use with a supply of gas; and said apparatus comprising:
means defining a chamber for containing the gas;
means for receiving and supporting the solid sample, said receiving and supporting means having a sample-abutting portion, and defining a sample-access opening that communicates with said chamber;
means for supplying a stream of the gas and for directing the stream toward said sample-access opening from within said chamber;
means for drawing the stream of gas away from the sample surface to flow along a first path, within the chamber, that is approximately normal to said sample-abutting portion of said sample receiving and supporting means;
means, including an anode positioned and arranged with respect to the chamber, for forming an electrical discharge, in the gas that is between said sample-access opening and said anode, to sputter the atoms out of the sample-surface for motion with the gas stream flowing away from the sample surface;
means for bending the stream of the gas flowing away from the sample surface, and the atoms in motion therewith, from said first approximately normal path into a second path that has an axis which is not approximately normal to said sample-abutting portion of said sample receiving and supporting means;
means for projecting a beam of light approximately along said axis, for passage through the gas stream flowing along said second path; and
means for detecting intensity of said light beam after passage through the gas stream;
wherein said bending means comprise a solid guide surface, at least a major portion of which is approximately continuously contoured, and which is disposed to define said first and second paths and to deflect the stream of the gas flowing from the sample surface, and the atoms in motion therewith, from said first path into said second path; and
wherein said guide surface further includes an aperture along said axis for passage of said beam of light between said projecting and detecting means via said second path.

9. The apparatus of claim 8, wherein;
said axis of said second path is approximately parallel to said sample-abutting portion of said sample receiving and supporting means.

10. The apparatus of claim 8, wherein:
said supplying and directing means comprise at least one jet arranged to be immediately adjacent the sample-access opening and arranged to point at a substantially nonzero angle to said sample-abutting portion of said receiving and supporting means;
whereby said supplying and directing means direct the stream toward the sample surface at a substantially nonzero angle with the surface.

11. Apparatus for sputtering atoms from a sample surface of a solid sample, for atomic-absorption or -fluorescence measurements, the sample surface having a periphery, and said apparatus being for use with a supply of gas; and said apparatus comprising:
means defining a chamber for containing the gas;
means for receiving and supporting the solid sample, said receiving and supporting means having a sample-abutting portion, and defining a sample-access opening that communicates with said chamber;
means for supplying a stream of the gas and for directing the stream toward the sample-access opening from within said chamber;
means for drawing the stream of gas away from the sample surface to flow along a first path, within the chamber, that is approximately normal to the sample-abutting portion of the receiving and supporting means;
means, including an anode, for forming an electrical discharge in the gas that is between the sample-access opening and said anode, to sputter the atoms out of the sample surface for motion with the gas stream flowing away from the sample surface;
means for bending the stream of the gas flowing away from the sample surface, and the atoms in motion therewith, from said first approximately normal path into a second path that is bifurcated, having two legs extending in mutually substantially opposite directions away from said first path, and that has an axis which is not approximately normal to the sample surface;
wherein in operation the stream flowing away from the sample surface splits into two substreams, each substream flowing along one of said two legs, respectively;
means for projecting a beam of light approximately along said axis, for passage through both substreams of the gas stream flowing along said second path; and
means for detecting said intensity of said light beam after passage through the gas stream.

12. Apparatus for making atomic-absorption measurements, said apparatus being for use with a solid sample and comprising:
means for receiving and supporting the solid sample, said receiving and supporting means defining a sample-sputtering port;

means for providing a stream of gas adjacent to said sample-sputtering port;

means, including an anode and a voltage supply, for forming an electrical current discharge, in said gas stream between said sample-sputtering port and said anode, to sputter atoms out of the solid sample into said gas stream to form a composite stream of gas and atoms;

means for projecting a beam of light through said composite stream and for detecting intensity of said beam after passage through said composite stream;

means for determining absorbance of said light beam by said composite stream, using said detected intensity of said beam after passage through said composite stream, said absorbance-determining means having a calibration curve which includes a portion that is approximately linear and at least one portion that is nonlinear; and automatic means, responsive to said absorbance-determining means, for substantially continuously adjusting current magnitude in said electrical current discharge to cause said determined absorbance to be in said approximately linear portion of said calibration curve, alleviating the necessity for selecting a spectral line of different sensitivity.

13. The apparatus of claim 12, wherein said projecting means and said determining means, considered together, comprise:

means for causing said determining means to respond to said beam of light over a spectral waveband of selectable nominal wavelength;

means for limiting said spectral waveband of said beam of light over which said determining means respond;

means for making a selection of said nominal wavelength; and means for varying said selection of said nominal wavelength of said beam of light substantially continuously while displaying or recording said absorbance.

14. The apparatus of claim 12, wherein:

said current-adjusting means comprise means for varying effective impedance of said voltage supply.

15. The apparatus of claim 14, wherein:

said impedance-varying means comprise a variable resistance that is effectively in series with said electrical current discharge.

16. Atomic-absorption apparatus for use with a solid sample and comprising:

means for receiving and supporting the solid sample, said receiving and supporting means defining a sample-sputtering port;

means for providing gas adjacent to said sample-sputtering port;

means, including an anode and a voltage supply, for forming an electrical current discharge, in said gas between said sample-sputtering port and said anode, to sputter atoms out of the solid sample into said gas to form a composite of gas and sample atoms;

means for projecting a beam of light through said composite and for detecting intensity of said beam after passage through said composite;

means for determining absorbance of said light beam by said composite, using said detected intensity of said beam after passage through said composite;

means for substantially continuously adjusting current magnitude in said electrical current discharge to hold said determined absorbance at a particular value; and utilization means for displaying or recording said current magnitude.

17. The apparatus of claim 16, wherein:

said current-adjusting means comprise means for varying effective impedance of said voltage supply.

18. The apparatus of claim 17, wherein:

said impedance-varying means comprise a variable resistance that is effectively in series with said electrical current discharge.

19. The apparatus of claim 16, wherein:

said utilization means comprise means for displaying a parameter derived from said current magnitude, as a measure of concentration of the sample.

20. The apparatus of claim 16, wherein:

said utilization means comprise means for recording a parameter derived from said current magnitude, as a measure of concentration of the sample.

21. The apparatus of claim 16, wherein said projecting means and said determining means, considered together, comprise:

means for causing said determining means to respond to said beam of light over a spectral waveband of selectable nominal wavelength;

means for limiting said spectral waveband of said beam of light to which said determining means respond;

means for making a selection of said nominal wavelength; and means for varying said selection of said nominal wavelength of said beam of light substantially continuously while displaying said discharge current amplitude, to display a spectrum related to an atomic-absorption spectrum of the sample.

22. The apparatus of claim 16, wherein said projecting means and said determining means, considered together, comprise:

means for causing said determining means to respond to said beam of light over a spectral waveband of selectable nominal wavelength;

means for limiting said spectral waveband of said beam of light to which said determining means respond;

means for making a selection of said nominal wavelength; and means for varying said selection of said nominal wavelength of said beam of light substantially continuously while recording said discharge current amplitude, to record a spectrum related to an atomic-absorption spectrum of the sample.

23. Apparatus for sputtering atoms from a sample surface of a solid sample for atomic-absorption or -fluorescence measurements, the sample surface having a periphery, and said apparatus being for use with a supply of gas; and said apparatus comprising:

means defining a chamber for containing the gas;

means for receiving and supporting the solid sample;

said receiving and supporting means comprising a cathode:

having a rear side positioned and arranged to receive and contact the periphery of the sample surface along a sample-abutting plane, and having a front side, and defining a cathode aperture that passes entirely through said cathode;

said chamber-defining means comprising a spacer fitted within said cathode aperture and:

having a rear side positioned near the sample-abutting plane and shaped to receive and contact the sample surface, and having a front side, and defining a spacer aperture that passes entirely through said spacer and communicates with the chamber interior, and defining a conduit for passage of the gas from the gas supply through said spacer aperture and toward said sample-abutting plane;

an anode positioned and arranged with respect to the chamber and having a rear side that faces said respective front sides of said cathode and spacer, and defining an anode aperture that is approximately aligned with said spacer aperture;

an insulator interposed between said cathode and anode; and a compliant member, interposed between said spacer and said anode, for urging said rear side of said spacer toward said sample-abutting plane and thereby toward the sample surface;

whereby in use said cathode and spacer both closely contact the sample surface despite normal production tolerances of said cathode, anode, insulator and spacer, and despite normal surface-finishing irregularities of the sample surface.

24. The apparatus of claim 23, wherein:
said compliant member is an O-ring.

25. The apparatus of claim 23, wherein:
said compliant member is an O-ring; and
an O-ring groove is formed in the back side of the anode to receive said O-ring.

26. The apparatus of claim 23, wherein:
said anode further comprises a gas-supply duct disposed to feed the gas to said conduit defined in said spacer.

27. The apparatus of claim 23:
wherein said electrical discharge generates heat that raises respective temperatures of the sample, said spacer, and said cathode;
further comprising means for lowering said temperature of said cathode to draw away said heat to cool the periphery of the sample surface.

28. Apparatus for sputtering atoms from a solid-sample surface and making atomic-absorption measurements with the atoms, said apparatus being for use with a supply of gas and comprising:

means defining an optical-measurement chamber;

means, including a sample-sputtering port, for receiving and supporting the solid sample so that the sample surface faces into said chamber at said sample-sputtering port;

means for substantially continuously directing a stream of the gas within said chamber from the gas supply toward said sample-sputtering port and thereby to the sample surface;

means, including an anode, for forming an electrical discharge, in the gas that is between said sample-sputtering port and said anode, to form ions of the gas and to bombard the sample surface with said ions to sputter atoms of the sample from the sample surface;

variable-speed means for substantially continuously drawing off the gas from said chamber;

means for projecting a beam of light through said sputtered atoms and for making measurements of optical absorbance by said sputtered atoms; and means for automatically controlling said speed of said drawing-off means to optimize said measurements of optical absorbance.

29. The apparatus of claim 28:
also comprising means for monitoring pressure within said chamber; and
wherein said speed-controlling means are responsive to said pressure-monitoring means to maintain pressure within said chamber at least approximately constant.

30. The apparatus of claim 28:
also comprising means for monitoring said measurements; and
wherein said speed-controlling means are responsive to said measurement-monitoring means to maintain said measurements in an optimum absorbance range.

31. Apparatus for sputtering atoms from a sample surface of a solid sample and making atomic-absorption measurements with such atoms, said apparatus being for use with a supply of gas and comprising:

means defining an optical-measurement chamber;

means, including a sample-sputtering port, for receiving and supporting the solid sample so that the sample surface faces into said optical-measurement chamber at said sample-sputtering port;

variable-rate means for substantially continuously directing a stream of the gas within said optical-measurement chamber from the gas supply toward said sample-sputtering port and thereby to the sample surface;

means, including an anode, for forming an electrical discharge, in the gas that is between said sample-sputtering port and said anode, to form ions of the gas and to bombard the sample surface with said ions to sputter atoms of the solid sample from the sample surface;

means for substantially continuously drawing off the gas from said optical-measurement chamber;

means for projecting a beam of light through sputtered atoms and for making measurements of optical absorbance by the sputtered atoms;

sensor means for monitoring a parameter that is related to quality of said measurements of optical absorbance; and means, responsive to said sensor means, for automatically controlling said rate of said variable-rate gas-directing means to optimize said measurements of optical absorbance.

32. The apparatus of claim 31, wherein:
said measurement-quality-related parameter is pressure within said optical-measurement chamber;
said sensor means comprise means for monitoring said pressure within said optical-measurement chamber; and
said rate-controlling means are responsive to said pressure-monitoring means to maintain said pressure within said optical-measurement chamber at least approximately constant, generally independently of spectral line in use for said measurements of optical absorbance.

33. The apparatus of claim 31, wherein:
said measurement-quality-related parameter is measured optical absorbance itself;
said sensor means comprise means for monitoring said measured optical absorbance; and
said rate-controlling means are responsive to said measured optical absorbance monitoring means, to maintain said measured optical absorbance in an optimum absorbance range, generally without necessarily selecting a different spectral line.

34. The apparatus of claim 31, wherein:
said quality of said measurements of optical absorbance in linearity of said measurements of optical absorbance, and said linearity of said measurements of optical absorbance varies with optical-absorbance range;
said measurement-quality-related parameter is measured optical absorbance itself;
said sensor means comprise means for monitoring said measured optical absorbance, and for determining therefrom said optical-absorbance range of said measured optical absorbance; and
the rate-controlling means are responsive to said optical-absorbance range determined by the sensor means, to maintain said measured optical absorbance in a relatively linear optical-absorbance range, generally without the necessity for selecting a less-sensitive spectral line.

35. Apparatus for sputtering atoms from a sample surface of a solid sample and for making atomic-absorption measurements using the atoms, comprising:
means for receiving and supporting the solid sample;
variable-rate means for sputtering atoms of the solid sample out of the sample surface;
means for projecting a beam of light through the sputtered atoms;
means for continuingly making absorbance measurements by determining intensity of said beam after passage through the sputtered atoms;
means, responsive to said measurement-making means, for developing measurement displays or recordings;
means for continuingly monitoring atomic emission from the sputtered atoms as an instantaneous indicator of rate of sputtering from the sample surface, including effects of fluctuations in variables that influence said rate of sputtering; and
means, responsive to said emission-monitoring means, for reducing effects of said fluctuations in said measurement displays or recordings.

36. The apparatus of claim 35, wherein:
said reducing means comprise means for automatically controlling said variable-rate means to maintain constant atomic emission;
whereby said sputtering rate is stabilized.

37. The apparatus of claim 35, wherein:
said reducing means comprise means for providing a signal related to said sputtering rate, for use in correcting said measurements for variations in said sputtering rate.

38. Apparatus for sputtering atoms from a sample surface of a solid sample that includes a matrix element, and for making atomic-absorption or -fluorescence measurements using the atoms; said apparatus comprising:
means for receiving and supporting the solid sample;
variable-rate means for sputtering atoms of the solid sample out of the sample surface;
means for projecting a beam of light through the sputtered atoms;
means for continuingly making absorbance measurements by determining intensity of said beam after passage through the sputtered atoms;
means, responsive to said measurement-making means, for developing measurement displays or recordings;
means for continuingly monitoring atomic emission from the sputtered atoms as an instantaneous indicator of rate of sputtering from the sample surface, including effects of fluctuations in variables that influence said rate of sputtering; and
means, responsive to said emission-monitoring means, for reducing effects of said fluctuations in said measurement displays or recordings;
said atomic-emission monitoring means comprising means for selectively monitoring intensity of atomic emission from the matrix element.

39. The apparatus of claim 38 wherein:
said selective intensity-monitoring means comprise means for selectively monitoring a single spectral line of the matrix element.

40. Atomic-absorption measurement apparatus for use with a sample, and comprising:
means defining an optical measurement chamber having windows for passage of a measurement light beam along a light path;
means for generating a stream of atoms of the sample within said optical measurement chamber; and
a baffle positioned and arranged within said optical measurement chamber and including a multiplicity of apertures, so that said baffle and said apertures are in and aligned with said light path.

41. The apparatus of claim 40, wherein:
said apertures in said baffle have a transverse aperture dimension of one-eighth inch or less.

42. The apparatus of claim 40, wherein:
said baffle has a honeycomb form.

43. The apparatus of claim 40, wherein:
said apertures in said baffle have a length-to-diameter ratio of roughly three.

44. The apparatus of claim 43, wherein:
said apertures in said baffle have a transverse aperture dimension of one-eighth inch or less.

45. A method for sputtering atoms from a solid sample and making atomic-absorption or -fluorescence measurements therewith, the sample having a bulk material and having an initially exposed surface, and the initially exposed surface having irregularities or impurities not representative of the bulk material; said method comprising the steps of:
striking a high-energy glow discharge against the initially exposed, the surface acting as a cathode of said discharge, and operating said glow discharge for a period of less than one minute to wear away the initially exposed surface and produce a fresh new surface of the sample that is representative of the bulk material; and
then operating a glow discharge at much lower energy against the fresh new surface to produce atoms of the sample for use in atomic-absorption or atomic-fluorescence measurements; and
while operating said glow discharge at said much-lower energy, measuring absorbance or fluorescence of the atoms.

46. The method of claim 45, wherein:
said high-energy glow discharge is pulsed at between approximately ten and approximately twenty hertz inclusive.

* * * * *